United States Patent [19]

Faulhaber et al.

[11] 4,390,785
[45] Jun. 28, 1983

[54] METHOD AND APPARATUS FOR REMOTELY DETECTING GASES IN THE ATMOSPHERE

[75] Inventors: Mark E. Faulhaber; James M. Prober, both of Wilmington, Del.

[73] Assignee: E. I. Du Pont de Nemours & Co., Wilmington, Del.

[21] Appl. No.: 220,997

[22] Filed: Dec. 29, 1980

[51] Int. Cl.³ ............................ H01J 31/49; G01J 1/00
[52] U.S. Cl. .................................... 250/330; 250/334; 250/339
[58] Field of Search ............... 250/330, 334, 339, 340, 250/343; 356/51, 407, 416, 418

[56] References Cited

U.S. PATENT DOCUMENTS

| | | | |
|---|---|---|---|
| 3,032,655 | 5/1962 | Romans | 250/43.5 |
| 3,143,648 | 8/1964 | Bradley et al. | 250/43.5 |
| 3,662,171 | 5/1972 | Brengman et al. | 250/83.3 H |
| 3,748,471 | 7/1973 | Ross | 250/333 |
| 3,783,284 | 1/1974 | McCormack | 250/339 |
| 3,821,553 | 6/1974 | French | 250/339 |
| 4,061,578 | 12/1977 | Kleinerman | 250/330 |
| 4,100,481 | 7/1978 | Gournay | 324/4 |
| 4,345,840 | 8/1982 | Goetz et al. | 250/339 |

OTHER PUBLICATIONS

D. I. Sebacher, Airborne Nondispersive Infrared Monitor for Atmospheric Trace Gases, Rev. Sci. Instrum. 49(11), pp. 1520-1525, 1978.

*Primary Examiner*—Alfred E. Smith
*Assistant Examiner*—Janice A. Howell

[57] ABSTRACT

Presence and location of infrared radiation-absorbing or emitting gases in the atmosphere can be ascertained by means of an infrared imaging-analyzing means which views a given scene and receives infrared radiation therefrom. Analytic and reference beams are produced, the latter having reduced sensitivity to the gas of interest, and are converted to electric signals, which are processed in real time to provide a signal corresponding to their ratio. This ratio signal is further processed to generate an image, which can be displayed and viewed. This technique is particularly suitable for surveying large areas for seepage of methane or other hydrocarbon gases from underground gas and/or oil deposits.

24 Claims, 2 Drawing Figures

METHOD AND APPARATUS FOR REMOTELY DETECTING GASES IN THE ATMOSPHERE

BACKGROUND OF THE INVENTION

This invention relates to a method and apparatus for remotely detecting the presence of certain gases in earth atmosphere and their location relative to fixed reference points on the ground.

Detection of hydrocarbon gases seeping from underground oil and gas deposits is of great importance to oil and gas prospectors. Other situations where the detection of a gas in the air is important include, for example, leaks in natural gas pipelines of underground gas lines as well as leaks of industrial gases or volatile materials from chemical reactors, storage tanks and railroad cars.

Various methods of gas detection are available. Most of those require sampling of air near the suspected leak or seepage area and gas analysis by a suitable technique. Detection methods which do not require sampling use, among others, infrared scanners, microwave reflection systems, or optical systems responsive to bioluminescence. An ideal technique should be sufficiently sensitive to detect trace gas concentrations in the air; sufficiently specific to reduce uncertainty as to the gas identity; and sufficiently versatile to be useful for remote surveying of both small, limited areas, such as a building or a pipe and large areas, such as a prospective oil field or plant site.

SUMMARY OF THE INVENTION

According to the present invention, there is provided a method and an apparatus for detecting the presence in the atmosphere of a gas which absorbs or emits infrared radiation within a defined wavelength region and determining its location with respect to at least one fixed background reference point, wherein:

(a) a number of points within a circumscribed background area, which are at a temperature different from the average temperature of the intervening atmosphere are viewed by the imaging optics of a dual sensor system imaging-analyzing means capable of generating electrical output signals that are responsive to the resulting net radiative flux transmitted through the atmosphere;

the first sensor system having a higher sensitivity and the second sensor system having a lower sensitivity to the gas of interest in the defined infrared wavelength region;

(b) the amplitudes of the output signals generated by said sensor systems are continuously or repeatedly ratioed within the defined infrared wavelength region; and (c) an image signal responsive to the ratio of said output signal amplitudes is produced, said image signal being displayed on a display means, the image indicating the presence of the gas of interest at one or more points within the circumscribed area being surveyed.

DETAILED DESCRIPTION OF THE INVENTION

A gas which can be detected according to the method of this invention must have at least one known characteristic infrared absorption or emission region which would permit its positive identification. As is well known, infrared absorption peaks are located at exactly the same wavelengths in a chemical compound's spectrum as its infrared emisson peaks. Thus, for example, methane has an infrared spectrum which contains a series of very sharp peaks between 7.2 and 8.2 $\mu$m. All of those peaks can be selected for the identification of methane. Other gases which have well defined infrared absorption or emission regions include, for example, ammonia, ethylene, propane, sulfur dioxide, and water.

Figure 1:
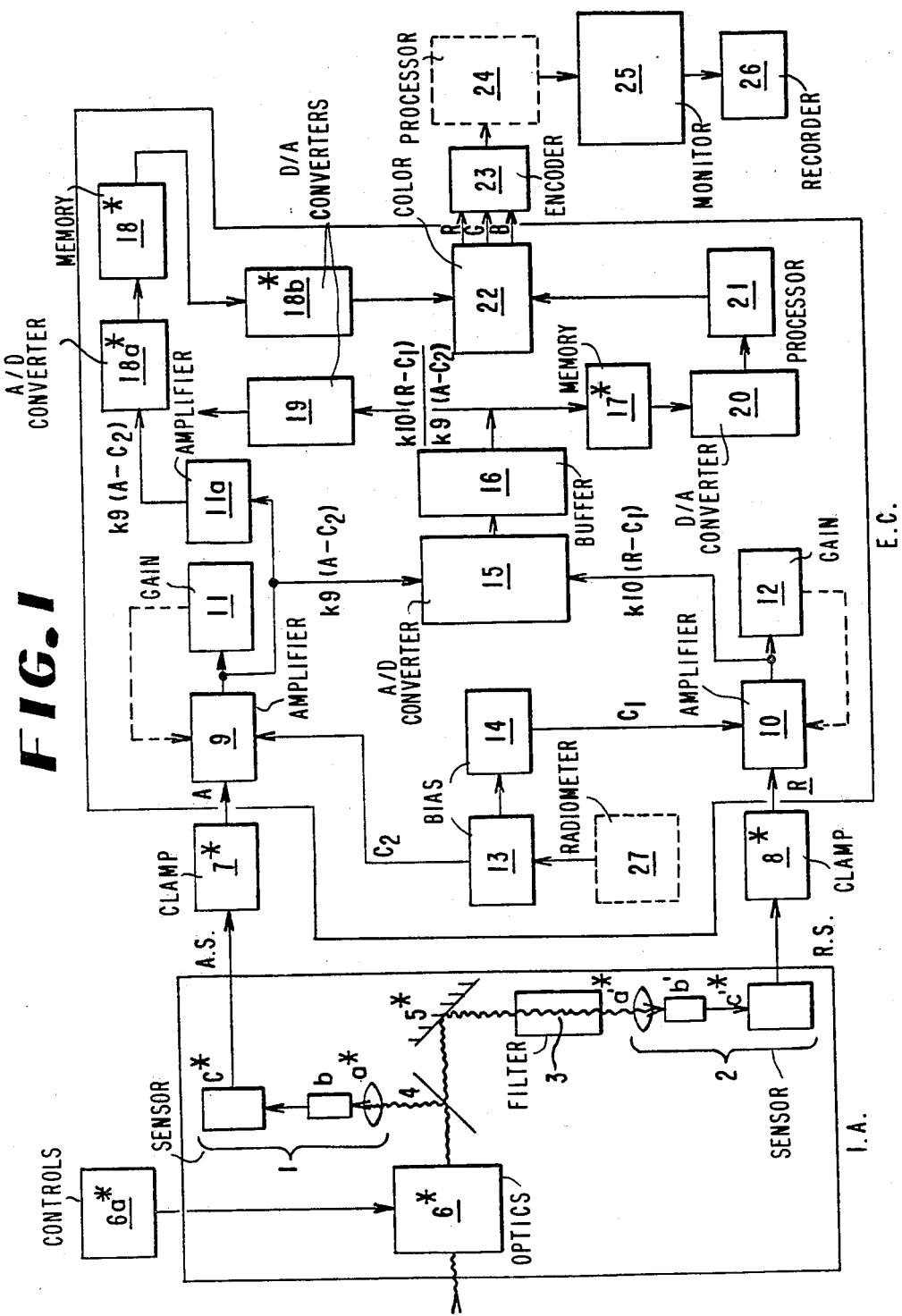
FIG. 1 is a block diagram of a suitable infrared imaging-analyzing means and its associated electronic equipment.

The equipment which is used in the practice of the present invention consists of a dual-detector infrared imaging-analyzing means and associated instrumentation. A block diagram of this equipment is shown in FIG. 1. Block I.A. schematically represents the essential parts of the preferred type of imaging-analyzing means, which are: analytic sensor means 1 consisting of lens a*, infrared detector b, and preamplifier c*; reference sensor means 2 consisting of lens a'*, infrared detector b', and amplifier c'*; gas filter 3; beam splitter 4; mirror 5*; and imaging optics 6*. The imaging-analyzing means I.A. can typically be a Model 210 dual-channel thermal imaging system of Inframetrics Inc., Bedford, Mass., modified by displacing the reference sensor means 2 along the incoming infrared beam path to allow space for gas filter 3. Furthermore, the original wavelength-selective beam splitter is replaced by a substantially spectrally neutral beam splitter which does not discriminate by wavelength. Beam splitter 4 is made of germanium and coated on one side with an antireflective material. This beam splitter reflects about 36% and transmits about 64% of incident light. Lenses a* and a'* are condensing lenses, which have a focal length of about 1 cm, so that they cause convergent beams to fall on the detector. Matched detectors b and b' are of the mercury-cadmium telluride type and have their highest sensitivity to infrared radiation within the 8–12 $\mu$m region. They are cooled with liquid nitrogen. Gas filter 3, which is inserted in the light path of the reference sensor system, normally would be filled with the gas of interest. However, a device such as, for example, a carousel containing a selection of reference gases may be installed instead. With such an apparatus, it is possible to determine the presence and location of two or more gases in turn. As a result of loss of some light intensity in the reference sensor system due to the filter as well as to a longer path, the amount of radiation which actually reaches the reference detector b' is about the same as that reaching the analytic detector b. Micrometer adjustable registration means (not shown) are used to bring the images of the scenes viewed by the detectors into exact coincidence. The imaging optics module 6* contains an opening for viewing the area of interest and a system of two oscillating mirrors, which convert a linear scan into a two-dimensional image. Normally, this module is equipped with a suitable lens, which may be of a fixed focal length or a zoom type. Imager control electronics module 6a* controls the scan rate and synchronization.

It has been found advantageous to design an electronic circuit, E.C., especially adapted to the needs of this invention, so that only certain electronic components of the original Inframetrics equipment have been retained and others have been added. The original Inframetrics components are indicated in FIG. 1 by an asterisk. This redesigned circuit includes clamps (D.C. restorer circuits) 7* and 8*, which convert an AC-coupled signal from detector output to a thermally adjusted reference signal; variable gain amplifiers 9 and 10; automatic gain controls 11 and 12; analytical bias level control 13; amplifier 11a; analog-to-digital (A/D) converter 18a*; reference bias level control 14; ratioing analog-to-digital (A/D) converter 15; buffer 16; scan inverter memories 17* and 18*; digital-to-analog (D/A) conveters 18b*, 19, and 20, wherein the ratio output at 19 can be used for testing, calibrating or adjusting the circuit's performance; signal processor 21; color formulator 22; color encoder 23; image processor 24 which is considered to be optional; video monitor 25; and video recorder 26. Optionally, a properly scaled temperature monitoring radiometer 27 may be connected to the bias level control 13.

Equipment not originally supplied with the infrared thermal scanner can be either obtained commercially or built from commercially available components. For example, color encoder 23, which converts red, green, and blue (RGB) inputs into the standard NTSC (National Television System Committee) signal, is LENCO model CCE 850. The color encoder 23 is required in this case because an NTSC TV monitor is used as a video display. The video monitor 25 is Sony PVM 8000 and the video recorder 26 is JVC CR-4400 LU.

In the practical operation of the method of the present invention, the imaging-analyzing means, I.A., and some or all of the associated electronic equipment, E.C., are mounted either in a stationary location or in an aircraft or ground vehicle. The imaging-optics is directed at the area under surveillance and receives the net infrared radiation absorbed or emitted by the intervening atmosphere and background such as buildings, water surfaces, and any objects or vegetation therein. Referring now to FIG. 1, the infrared image is scanned pixel by pixel by a beam formed in the optics module 6*. The scanning beam is then split into two beams, one which is reflected to sensor means 1 and the other one transmitted and reflected to sensor means 2 by beam splitter 4 and mirror 5*, respectively. Since the transmitted beam passes through gas filter 3, which contains the gas of interest, a portion of the total radiation that is transmitted by the beam splitter is attenuated in the region of the infrared absorption of the gas of interest. The baseline of the signal exiting the analytic sensor means 1, A.S., and the signal exiting the reference sensor means 2, R.S., are first independently thermally compensated by clamps 7* and 8* to a repetitive, reference flag level signal. Each D.C restored signal is further biased by subtracting at the input terminal of variable gain amplifiers 9 and 10 an empirically determined constant value furnished by controls 13 and 14. The biased signals are then passed through automatic gain controls 11 and 12, respectively. Ratioing A/D converter 15 generates a ratio of the biased analytic and reference signals in digital form. After passing first through buffer 16, the digitized ratio signal is split into two paths. A first portion is reconverted back to analog form in D/A converter 19. A monitoring device (not shown) may be attached at the output of converter 19, if desired. The other portion passes to the scan converter memory 17* and is then changed from the digital to analog form by converter 20 for input to signal processor 21. Meanwhile a portion of the biased analytic output signal is input to the scan converter memory 18* via amplifier 11a and converter 18a*. After conversion by D/A converter 18b*, the output signal from D/A converter 18b*, and the ratio output signal from signal processor 21 are combined in color formulator 22. This circuit prepares for display the sum of these two signals as functions of the intensity levels of the selected red, blue, and green colors.

The overall function of the electronic equipment associated with the thermal imaging system is to automatically regulate the average or, optionally, peak amplitudes of the analytic and reference signals and compute the pixel-by-pixel instantaneous ratios of the images generated in the imaging system unit shown as block I.A. in FIG. 1, to produce a composite image signal which is indicative of both the location and concentration of the gas of interest. However, processing of the image signals does not necessarily have to take place at the same instant as their formation. The signals may be recorded and processed at a different time or location.

Figure 2:
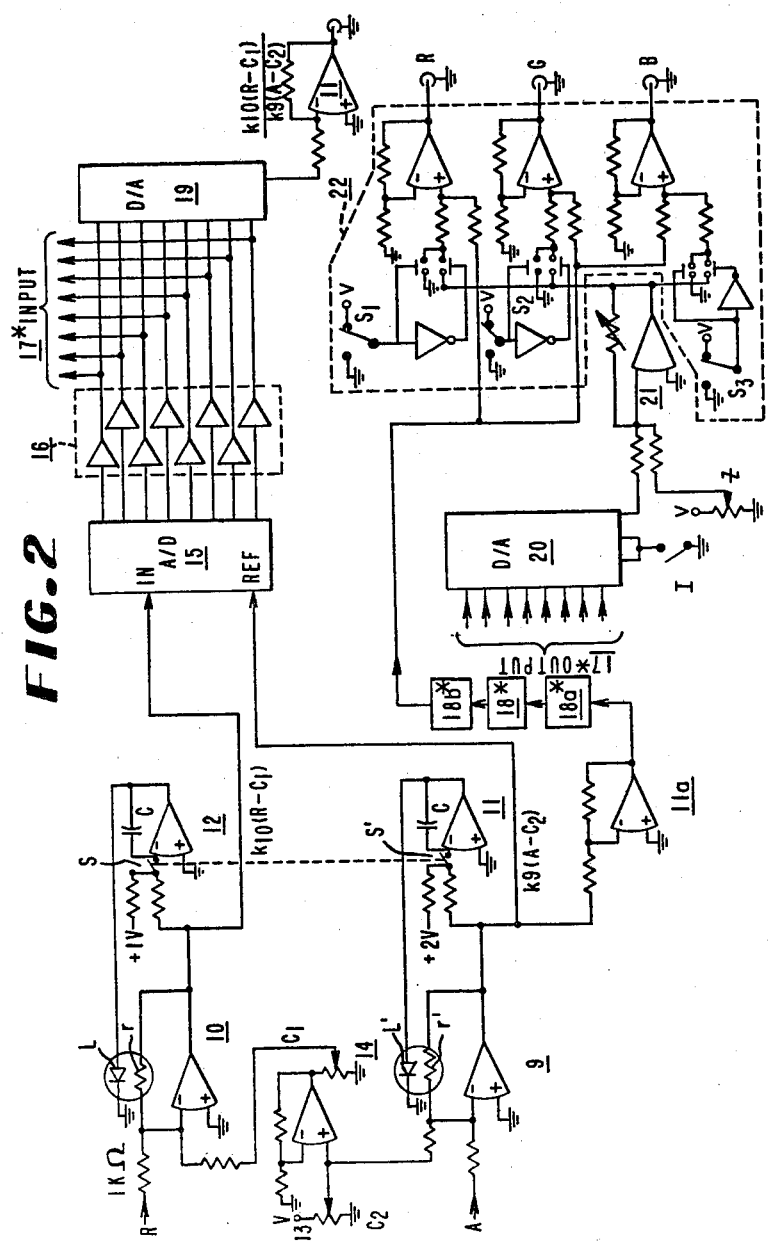
FIG. 2 is a circuit diagram of certain electronic components indicated as numbered blocks in FIG. 1.

Referring now to FIGS. 1 and 2, the signal from sensor means 2 is transmitted, via the line marked R.S. in FIG. 1, to clamping circuit 8* (not shown in FIG. 2), where it is amplified and clamped to a reference flag temperature. (Clamping circuits are well known in the art, and therefore no further description will be provided of block 8*.) In general, a clamping circuit references a waveform to a given potential. The amplitude of the clamped signal leaving block 8* is approximately 10 mV/°C., which is input to block 10, via the line marked R in FIG. 1. Block 10, shown in greater detail in FIG. 2, is known in the art as an inverting-adder variable gain operational amplifier. Principally, it comprises a resistor R in its feedback circuit whose value changes depending upon the brightness of light-emitting diode L. Also input to amplifier 10 is a constant voltage proportional to the potentiometer settings $C_2$ and $C_1$, represented by blocks 13 and 14, respectively in FIG. 1. The voltage level selected for input to these cascaded potentiometers (FIG. 2) was selected to cover the expected temperature ranges and approximate the effect of the radiometer block 27 (FIG. 1), intended to compensate for an effect of the intervening atmosphere to be described later. The proper settings of $C_2$ and $C_1$ are obtained empirically by adjusting the potentiometers while viewing the image at a scene having in it no gas of interest. The output of variable gain amplifier 10 is $K_{10}(R-C_1)$, where R is the reference signal; $C_1$ is the bias voltage from potentiometer block 14; and $K_{10}$ is the instantaneous gain of amplifier 10 which is determined by the ratio of the values of feedback-connected photoresistor r and the 1KΩ input resistor. This output signal voltage is compared against a constant +1 volt reference signal at the inverting terminal of operational amplifier 12 to obtain a difference signal. Operational amplifier 12, which is configured as an integrator, controls the automatic gain control loop. It integrates the difference signal and applies the resultant output voltage to vary the current through light-emitting diode L, which in turn changes the value of photoresistor r until the output of amplifier 10 averages −1 volt. Time averaging of the automatic gain control signal, effected by amplifier 12, will occur at a rate defined by the value of integrating feedback capacitor C (FIG. 2).

In like manner, variable gain amplifier 9 receives the signal from the analytic-detector channel, via the line marked A.S. in FIG. 1 and the thermal clamping circuit 7* (part of the commercial unit, and not shown in FIG. 2). Amplifier 9 also receives bias voltage signal $C_2$ from potentiometer 13 (FIG. 1). Amplifier 9 is also an operational amplifier, with a similar feedback circuit, including resistor r' and light emitting diode L'. Similarly, operational amplifier 11 functions as an integrator with capacitor C' to provide automatic gain control. Thus, the signal $(A-C_2)$ is amplified by amplifier 9 as a function of gain $K_9$ until it averages $-2$ volts, where A is the signal from the analytic detector and $C_2$ the voltage from block 13. Signals $K_{10}(R-C_1)$ and $K_9(A-C_2)$ are input to the IN and REF terminals, respectively, of A/D converter 15 (a commercial unit of TRW Corporation, Model TDC 1007J) and produces a digital output proportional to $K_{10}(R-C_1)/K_9(A-C_2)$. This ratio signal is buffered by block 16, which comprises non-inverting digital power drivers, before it is sent to memory 17*. Memory 17* serves to scan-convert this ratio signal from a reciprocating scanned signal to a raster-scanned signal. The ratio is monitored by D/A 19 (a TRW Corp, unit, Model TDC 1016J), whereas Memory 17* output is converted by D/A converter 20 into an analog voltage for use by color formulator 22 after amplification by amplifier 21. The signal $K_9(A-C_2)$ is similarly amplified by amplifier 11a and converted to digital form by A/D converter 18a* (typically TRW Corp. Unit Model TDC 1014J) for loading into memory 18*.

When the gas of interest occupies a large portion of the scene, the automatic gain control (AGC) will tend to reduce the sensitivity of the equipment to changes in gas concentration. Improved performance of the analyzer can be obtained by opening coupled switches S and S' in the feedback loops at the input terminals of integrators 11 and 12, respectively.

When the gas of interest is absent, the output of D/A 20 usually will be a constant other than zero. The zero control Z of amplifier 21 is used to null this constant and thus to zero-adjust the analyzer.

The output of memory 18*, converted by a digital to analog converter 18b* is tied into amplifiers 22, as equal inputs to the Green, Red and Blue color-encoder input terminals. When the presence of gas causes a change of the ratio $K_{10}(R-C_1)/K_9(A-C_2)$, the contribution of the gas signal can be selectively set by switches $S_1$, $S_2$, and $S_3$ to any color input. Invert-control I on D/A 20 helps the viewer to specify the location of the gas in the image by providing either positive or negative deviation about the ratio zero-set value.

Since the arrangement of blocks 23-26 in FIG. 1 is optional, and since their functions have already been discussed above, they are not shown in FIG. 2.

The image of the terrain, which is received from scan converter memory 18*, is encoded as a gray scale image, while the ratio output from signal processor 21 can be encoded in color so that a cloud corresponding to the gas of interest appears on the screen of monitor 25 superimposed on the topographic picture of the terrain. The color intensity of the gas cloud will roughly correspond to the gas concentration in the atmosphere.

As an alternative to imaging, the raw A and R signals at the output terminals of clamps 7* and 8*, respectively, can be separately biased and averaged over a number of image frames. The ratio of the averaged signals $(\overline{A-C_2})/(\overline{R-C_1})$ can then be observed on a meter or converted to an audio signal indicating the presence of the gas.

It is to be noted that, instead of gas filter 3 placed next to the reference sensor system 2, one can have one or more interference filters placed in either sensor system or different interference filters placed in each sensor system. Although each filtering system will produce a different result, the net effect will be the same, that is, one sensor system will have greater sensitivity than the other to the gas of interest within the defined infrared wavelength region. The infrared wavelength region is chosen for each gas of interest so that the gas has a significant characteristic infrared spectral absorption or emission within that region. It may cover the complete infrared range for the gas of interest or only a portion of it, usually that where the characteristic infrared spectral emission or absorption of the gas of interest is the strongest.

The detection method of the present invention is based on the following theoretical considerations:

It shall be assumed that the background (e.g., earth surface, buildings, or bodies of water) and the intervening atmosphere between the background and the infrared radiation detection system are potentially at different but uniform temperatures. An above-ground sensor will receive radiation from three sources: the background emission, radiation reflected from the background, and intervening atmosphere emission or absorption (plus scattering). The total apparent radiance, L, reaching the analyzer for a given field of view can be expressed by the following equation (1):

$$L = \frac{1}{\pi} \int_0^\infty \{\tau(\lambda)\epsilon(\lambda)M_\lambda + \tau(\lambda)[1-\epsilon(\lambda)]E_\lambda(\text{sky}) + [1-\tau(\lambda)]M_\lambda(\text{air})\}d\lambda \quad (1)$$

$$Wcm^{-2}sr^{-1}$$

where:

$\lambda$ is the wavelength;

$\tau(\lambda)$ is the spectral transmittance of the intervening atmosphere;

$\epsilon(\lambda)$ is the spectral emissivity of the non-black body background;

$M_\lambda$ is the spectral radiant emittance of a black body at the temperature of the background; $W/cm^2/\mu m$;

$E_\lambda(\text{sky})$ is the downwelling spectral irradiance of the object under observation; $W/cm^2/\lambda m$; and $M_\lambda(\text{air})$ is the spectral emittance of a black body at the temperature of the intervening atmosphere; $W/cm^2/\lambda m$.

According to Beer's law:

$$\tau(\lambda) = e^{-k(\lambda)ct} \quad (2)$$

where $k(\lambda)$ is the absorption coefficient of the intervening atmosphere;

c is the concentration of the absorbing medium; and t is the path length of the intervening atmosphere.

Substituting the above exponential term for $\tau(\lambda)$ in equation (1), one gets:

$$L = \frac{1}{\pi} \int_0^\infty \{M_\lambda(\text{air}) + [M_\lambda - M_\lambda(\text{air})] - r(\lambda)(M_\lambda - E_\lambda(\text{sky}))]e^{-k(\lambda)ct}\}d\lambda \quad (3)$$

where $r(\lambda) = 1 - \epsilon(\lambda)$ = the background reflectivity. This is so because the conservation of energy requires $r(\lambda) + \alpha(\lambda) + \tau(\lambda) = 1$, where $\alpha(\lambda)$ is the absorptivity. Furthermore, from Kirchhoff's law, $\alpha(\lambda) = \epsilon(\lambda)$ and for an opaque background, $\tau(\lambda) = 0$.

The above equation (3) can be written in the following form:

$$L = K + \int_0^\infty I_\lambda e^{-k(\lambda)ct} d\lambda \tag{4}$$

where $I_\lambda$ is a function which includes the background image, while K is a function of air temperature only.

Equation (4) can be approximated by $$L = K + I e^{-\bar{k}ct} \tag{5}$$

where $\bar{k}$ is the effective average absorption coefficient, and I is the effective average value of $I_\lambda$.

With a dual channel imager-analyzer of the type described above, where the analytic channel is sensitive to the absorbing medium (i.e., $\bar{k} >> 0$), and the reference channel is insensitive to the same absorbing medium (i.e., $\bar{k} \approx 0$), equation (5) can be expressed as follows for each channel:

Analytic: $L_A = K_A + I_A e^{-\bar{k}ct}$ (6)

and Reference: $L_R = K_R + I_R$ (7)

Rearranging equations (6) and (7) and dividing the former by the latter, one has:

$$\frac{L_A - K_A}{L_R - K_R} = \frac{I_A e^{-\bar{k}ct}}{I_R} \tag{8}$$

Since the emittance and irradiance terms vary slowly and essentially in synchronism with one another with respect to a chosen scene we can assume that $$I_A = fI_R \tag{9}$$

where f is a constant.

Finally, substituting equation (9) into equation (8), one obtains:

$$\frac{L_A - K_A}{L_R - K_R} = f e^{-\bar{k}ct} \tag{10}$$

Since this biased relationship is independent of the image terms $I_A$ and $I_R$, it becomes now a function only of concentration and path length, ct.

Since the K terms are dependent on air temperature, this information can be supplied by a radiometer aimed at the air in a highly absorbing wavelength region. Under controlled conditions, when the air temperature does not change much over a short period, it is possible to replace the radiometer with a constant, which can be determined separately or automatically, as part of the measurement. The electronic equipment illustrated in FIGS. 1 and 2 permits operation without a radiometer using a preset bias voltage value, V.

The net effect of biasing the radiance signal is to provide for a more complete removal of all but the atmospheric absorption or emission effects.

It is not necessary for the purpose of this invention that the temperature of the background always be higher than the average temperature of the intervening atmosphere; the average temperature of the intervening atmosphere may equally well be higher than that of the background, and the only difference in the result will be the change of polarity of the output signals produced by the sensor systems. The present technique is sensitive to infrared radiation whether absorbed or emitted by the gas of interest. The imaging requirement is merely the existence of a temperature difference between the background and the atmosphere containing the gas.

The imaging-analyzing means will be usually transported by a slow plane or a helicopter over the target area at an altitude at which the concentration of the gas of interest is sufficiently high and the interference of water vapor in the air sufficiently low for this analytical technique to provide reasonably accurate and meaningful results. As more advanced equipment becomes available, for example, focal plane array detectors, surveillance overflights at high altitudes may be feasible. The present equipment is capable of detecting temperature differences of about 0.2° C. This, naturally, may be further refined as more advanced equipment becomes available. Presently, meaningful data can be obtained for temperature differences between the background and the intervening atmosphere as small as 1°-2° C.

The present equipment uses gas filter cells to provide the reference signal. It is possible that in the future such cells may be replaced by calibrated interference filters or by other devices. The presently used gas filter cells are 6 cm long, but a longer or shorter cell may be more practical for a particular application. Similarly, depending on the infrared absorption intensity of the reference gas, it may sometimes be practical to use the gas at a 100% concentration or to dilute it with another gas, for example, nitrogen. Such adjustments and modifications are based on determining the point of maximum sensitivity to changes in the value of the analytical-to-reference output signal ratio for each particular gas species to be analyzed. Further, it is possible to use two separate, single channel, time-synchronized imaging means instead of dual channel equipment. Those separate imaging means would produce, respectively, a reference signal and an analytic signal at identical times over the same field of view.

All such alternate embodiments are within the scope of this invention.

EXAMPLE

The operation of the imager-analyzer has been verified by observing the release of ethylene gas from a charged cylinder. The above-described equipment was used, the imaging means being first placed on a loading platform about 2 m off the ground. Gas released through the cylinder regulator was led through an 8 m long rubber hose having an inside diameter of 0.02 m, to a black-painted, stainless steel, 0.6 m diameter funnel, with its apex turned downward. The funnel was placed on the asphalt pavement below at a horizontal distance of 4 m from the imaging means. The gas pressure was maintained at 410 kPa, yielding an ethylene flow rate of 1.5 l/sec. The average gas concentration was 1.5% V/V at a point 12 cm above the funnel, close to ambient air temperature. The funnel itself was warmer than the ambient air. The air temperature was 27° C., and the asphalt pavement temperature about 35° C. The sky was partly cloudy.

The reference optics contained a 6 cm infrared-transmitting gas cell, which was charged with a mixture of equal volumes of ethylene and nitrogen. Red color was selected for displaying the analytic/reference ratio image, and the gain of the ratio image was adjusted to five times the analytic image. Bias levels were adjusted to almost extinguish the detector noise from the ratio signal.

With ethylene gas flow shut off, the funnel was clearly visible on the viewing screen as the background image. With gas flow on, a red image of the gas superimposed on the background image was clearly evident. With gas flow off again, the slow dissipation of the gas from the funnel was readily observed.

The imaging means was next moved to the ground level to view the funnel, about 4 m away, against the sky background.

When the gas flow was off, the funnel was clearly visible on the viewing screen. With the gas flow on, no gas image could be observed above the funnel because the temperature of the ambient air immediately above the funnel and of background ambient air was about the same. However, ethylene gas which swirled downward between the funnel and the imaging means was visible on the screen. Here, the warmer funnel provided suitable background for image formation.

We claim:

1. A method of detecting the presence in the atmosphere of a gas which absorbs or emits infrared radiation within a defined wavelength region and determining its location with respect to at least one fixed background reference point, wherein (a) a number of points within a circumscribed background area, which are at a temperature different from the average temperature of the intervening atmosphere are viewed by the imaging optics of an imaging-analyzing means having a first sensor means and a second sensor means capable of generating electrical output signals that are responsive to the resulting net radiative flux transmitted through the atmosphere;
    the first sensor means having a higher sensitivity and the second sensor means having a lower sensitivity to the gas of interest in the defined infrared wavelength region;
    (b) the amplitudes of the output signals generated by said sensor means are ratioed pixel-by-pixel within the defined infrared wavelength region; and
    (c) an image signal responsive to the ratio of said output signal amplitudes is produced, said image signal being displayed on a display means, the image indicating the presence of the gas of interest at at least one point within the circumscribed area being surveyed.

2. The method of claim 1 wherein the sensitivity of one of the sensor means to the gas of interest is reduced by placing in the path of infrared radiation reaching said sensor means a gas filter cell containing said gas of interest.

3. The method of claim 1 wherein the sensitivity of one of the sensor means to the gas of interest is altered by placing in the path of infrared radiation reaching said sensor at least one interference filter.

4. A method of claim 1 wherein the amplitudes of the output signals are ratioed continuously.

5. The method of claim 1 wherein the amplitudes of the output signals are ratioed repeatedly.

6. The method of claim 1 wherein the analysis is performed in real time.

7. The method of claim 1 wherein the gas of interest is a hydrocarbon.

8. The method of claim 7 wherein the gas is a member of the class consisting of methane and ethylene.

9. The method of claim 7 wherein the imaging-analyzing means is transported in an aircraft over areas of gas seepage.

10. The method of claim 1 wherein the presence and location of at least two gases is determined in turn, an appropriate filter being placed in the path of one of the infrared beams before it reaches the sensor means.

11. The method of claim 10 wherein two time-synchronized single channel imaging-analyzing means view the same scene, one of said means providing analytic data and the other reference data.

12. The method of claim 10 wherein a dual channel imaging-analyzing means equipped with a beam splitter which does not discriminate by wavelength is used to provide analytic and reference infrared radiation beams.

13. The method of claim 10 wherein the filter is a gas filter.

14. The method of claim 10 wherein the filter is an interference filter.

15. An apparatus for detecting the presence and determining the location of an infrared radiation-absorbing or emitting gas in the atmosphere, said apparatus comprising:

(1) an infrared imaging-analyzing means capable of viewing a circumscribed background area, receiving infrared radiation therefrom, producing in real time an analytic beam and a reference beam, and sensing said beams with two separate sensor means, one sensor means having greater sensitivity to the gas of interest than the other;
    (2) signal processing means for ratioing pixel-by-pixel the amplitudes of said reference and analytic signals; and
    (3) means for producing an image corresponding to the results of said ratioing.

16. An apparatus of claim 15 wherein analytic and reference infrared beams are produced by means of a beam splitter which does not discriminate by wavelength.

17. An apparatus of claim 15 which contains two separate time-synchronized single-channel imaging-analyzing means viewing the same circumscribed area.

18. The apparatus of claim 15 wherein the signal processing means comprises an automatic gain control circuitry for maintaining constant the long term amplitude values of the analytic and reference signals.

19. The apparatus of claim 15 wherein the signal processing means comprises an analog-to-digital converter for generating a point-by-point ratio of the amplitudes of the reference and analytic signals.

20. An apparatus of claim 15 wherein the values of the analytic and reference signals are biased by constants $C_1$ and $C_2$, which are voltage values obtained when the gas of interest is absent from the scene being viewed.

21. An apparatus of claim 20 wherein the values of $C_1$ and $C_2$ can be varied by means of the output of a radiometer.

22. An apparatus of claim 15 wherein the removal of a portion of infrared radiation from the reference beam is accomplished by placing in the path of said beam a filter.

23. The apparatus of claim 22 wherein the filter is a gas filter.

24. The apparatus of claim 22 wherein the filter is an interference filter.

* * * * *